(12) United States Patent
Okawa et al.

(10) Patent No.: US 9,888,836 B2
(45) Date of Patent: Feb. 13, 2018

(54) ENDOSCOPE

(71) Applicant: OLYMPUS CORPORATION, Tokyo (JP)

(72) Inventors: Fumiyuki Okawa, Tama (JP); Hidenori Hashimoto, Sagamihara (JP); Yasunori Matsui, Nishitokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/214,500

(22) Filed: Jul. 20, 2016

(65) Prior Publication Data

US 2016/0324406 A1 Nov. 10, 2016

Related U.S. Application Data

(63) Continuation of application No. PCT/JP2015/075519, filed on Sep. 8, 2015.

(30) Foreign Application Priority Data

Dec. 4, 2014 (JP) .................................. 2014-246137

(51) Int. Cl.
*A61B 1/04* (2006.01)
*A61B 1/05* (2006.01)
(Continued)

(52) U.S. Cl.
CPC .......... *A61B 1/051* (2013.01); *A61B 1/00009* (2013.01); *A61B 1/04* (2013.01);
(Continued)

(58) Field of Classification Search
CPC .... A61B 1/045; A61B 1/051; G02B 23/2484; H04N 5/341; H04N 5/3765; H04N 5/3658; H04N 5/3655
(Continued)

(56) References Cited

U.S. PATENT DOCUMENTS 4,396,951 A * 8/1983 Tanaka ................. H04N 5/2351 348/245
4,580,168 A * 4/1986 Levine ................. H04N 5/2173 348/244
(Continued)

FOREIGN PATENT DOCUMENTS

JP 2004-153677 A 5/2004
JP 2009-239383 A 10/2009
(Continued)

OTHER PUBLICATIONS

International Search Report dated Nov. 10, 2015 issued in PCT/JP2015/075519.

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An endoscope includes: a CMOS image sensor including only a vertical OB pixel region as an optical black pixel region, and a horizontal OB pixel region generation processing section that reads a photoelectric conversion signal generated in an effective pixel region in the CMOS image sensor and an OB signal generated in the vertical OB pixel region, adds the OB signal generated in the vertical OB pixel region to the beginning or end of each row of the photoelectric conversion signal which has been generated in the effective pixel region and read out for each row, and outputs a signal to which the OB signal is added.

7 Claims, 12 Drawing Sheets

(51) Int. Cl.
  *H04N 5/341* (2011.01)
  *H04N 5/361* (2011.01)
  *H04N 5/374* (2011.01)
  *H04N 5/378* (2011.01)
  *A61B 1/00* (2006.01)
  *G02B 23/24* (2006.01)
  *H04N 5/376* (2011.01)
  *H04N 5/225* (2006.01)

(52) U.S. Cl.
  CPC ......... *G02B 23/2484* (2013.01); *H04N 5/341* (2013.01); *H04N 5/361* (2013.01); *H04N 5/374* (2013.01); *H04N 5/378* (2013.01); *H04N 5/3765* (2013.01); *H04N 2005/2255* (2013.01)

(58) Field of Classification Search
  USPC .................................................. 600/109, 160
  See application file for complete search history.

(56) References Cited

U.S. PATENT DOCUMENTS

| | | | | |
|---|---|---|---|---|
| 4,860,095 | A * | 8/1989 | Kimura | A61B 1/05 348/241 |
| 4,891,695 | A * | 1/1990 | Uchikubo | A61B 1/042 348/581 |
| 4,979,035 | A * | 12/1990 | Uehara | H04N 5/335 348/76 |
| 5,196,939 | A * | 3/1993 | Elabd | H04N 3/14 348/244 |
| 5,717,457 | A * | 2/1998 | Morimoto | H04N 5/361 348/241 |
| 6,635,011 | B1 * | 10/2003 | Ozawa | A61B 1/00096 348/E5.029 |
| 7,315,327 | B2 * | 1/2008 | Kubota | H04N 5/2251 348/241 |
| 7,679,659 | B2 * | 3/2010 | Kobayashi | H04N 5/361 348/243 |
| 7,978,240 | B2 * | 7/2011 | Kido | H04N 5/23245 348/228.1 |
| 8,436,928 | B2 * | 5/2013 | Ise | H04N 5/232 348/241 |
| 8,520,101 | B2 * | 8/2013 | Meng | H04N 5/361 348/241 |
| 8,648,939 | B2 * | 2/2014 | Okuno | H01L 27/14609 348/241 |
| 2002/0021356 | A1 * | 2/2002 | Nakashima | A61B 1/00096 348/65 |
| 2002/0033891 | A1 * | 3/2002 | Ying | H04N 5/18 348/241 |
| 2003/0128285 | A1 * | 7/2003 | Itoh | H04N 5/367 348/246 |
| 2004/0061776 | A1 * | 4/2004 | Mochida | H04N 5/335 348/65 |
| 2004/0090547 | A1 * | 5/2004 | Takeda | H04N 5/361 348/241 |
| 2004/0183928 | A1 * | 9/2004 | Tay | H04N 5/361 348/244 |
| 2005/0083419 | A1 * | 4/2005 | Honda | H04N 5/361 348/244 |
| 2009/0091641 | A1 * | 4/2009 | Hattori | H04N 5/361 348/241 |
| 2009/0244338 | A1 * | 10/2009 | Kume | H04N 5/3575 348/294 |
| 2010/0026860 | A1 * | 2/2010 | Oshima | H04N 5/361 348/243 |
| 2011/0317055 | A1 * | 12/2011 | Nozaki | H04N 5/361 348/308 |
| 2012/0201433 | A1 * | 8/2012 | Iwasaki | A61B 1/00009 382/128 |
| 2014/0228638 | A1 * | 8/2014 | Ashida | A61B 1/00009 600/109 |
| 2014/0307073 | A1 * | 10/2014 | Ogasawara | H04N 7/18 348/75 |
| 2016/0213238 | A1 * | 7/2016 | Adachi | H04N 5/361 |

FOREIGN PATENT DOCUMENTS

| | | | |
|---|---|---|---|
| JP | 2011-055336 A | | 3/2011 |
| JP | 2011055336 A | * | 3/2011 |
| JP | 2011-206334 A | | 10/2011 |
| JP | 2013-126002 A | | 6/2013 |

\* cited by examiner

ENDOSCOPE

CROSS REFERENCE TO RELATED APPLICATION

This application is a continuation application of PCT/JP2015/075519 filed on Sep. 8, 2015 and claims benefit of Japanese Application No. 2014-246137 filed in Japan on Dec. 4, 2014, the entire contents of which are incorporated herein by this reference.

BACKGROUND OF THE INVENTION

1. Field of the Invention

The present invention relates to an endoscope that employs an image pickup device having only a vertical optical black pixel region.

2. Description of the Related Art

Conventionally, endoscopes provided with an image pickup device have been widely used in medical fields and industrial fields. Further, a technology for configuring an endoscope system has been known in which a signal processing apparatus, what is called a processor, is detachably connected with an endoscope to perform various kinds of signal processing related to the endoscope.

In addition, an image pickup device such as a CCD image sensor which is mounted to the endoscope of such a type includes, as is known, an effective pixel region where light is actually received and electric charge is obtained by photoelectric effects, and an optical black pixel region (OB region) provided around the effective pixel region, for performing offset detection of the electric charge including dark current.

Generally, the pixels in the image pickup device have characteristics in which, when the respective pixels have heat, electric charge is accumulated even if the pixels are not irradiated with light, and what is called dark current noise is generated.

The above-described optical black pixel region is arranged in the peripheral portion of the image pickup device in an optically-masked state. As a result, the optical black pixel region is not irradiated with light. Therefore, detection of the black level in the optical black pixel region enables the detection of only offset information of the electric charge including dark current noise and the like, and subtraction of the black level from the pixel information of the effective pixel region enables generation of an image pickup signal with the signal level of the OB pixels as a reference.

The above-described black level is defined as described below. The level of the output signals (optical black signals) from the optical black pixel region is clamped to a predetermined target level by what is called OB clamp processing and the average value of all the optical black signals obtained with the clamp level as a reference is defined as the black level, (See Japanese Patent Application Laid-Open Publication No. 2011-55336).

In recent years, also an endoscope that employs a CMOS image sensor as an image pickup device has been proposed. Due to the influence of recent size-reduction of image pickup device chips, such a CMOS image sensor has a size limitation depending on the type thereof, and includes the optical black pixel region only in the vertical direction in the pixel array region (includes only the vertical OB pixel region).

Furthermore, in a processor adaptive to an endoscope to which a CCD image sensor is mounted as an image pickup device (hereinafter, referred to as CCD adaptive processor), OB clamp processing geared to the horizontal optical black pixel region (horizontal OB pixel region) of the CCD image sensor is generally performed.

SUMMARY OF THE INVENTION

An endoscope according to one aspect of the present invention includes: an image pickup device including an effective pixel region in which a plurality of pixels capable of photoelectrically converting light to generate a photoelectric conversion signal are provided in a matrix shape, and a vertical optical black pixel region provided in at least one of an upper portion or a lower portion with respect to a scanning direction of the effective pixel region; a reading section that reads the photoelectric conversion signal generated in the effective pixel region in the image pickup device and an optical black signal generated in the vertical optical black pixel region in the image pickup device; and an output section that adds the optical black signal generated in the vertical optical black pixel region to each row of the photoelectric conversion signal which has been generated in the effective pixel region and read for each row by the reading section, and outputs a signal to which the optical black signal is added.

DETAILED DESCRIPTION OF THE PREFERRED EMBODIMENTS

Hereinafter, embodiments of the present invention will be described with reference to drawings.

Figure 1:
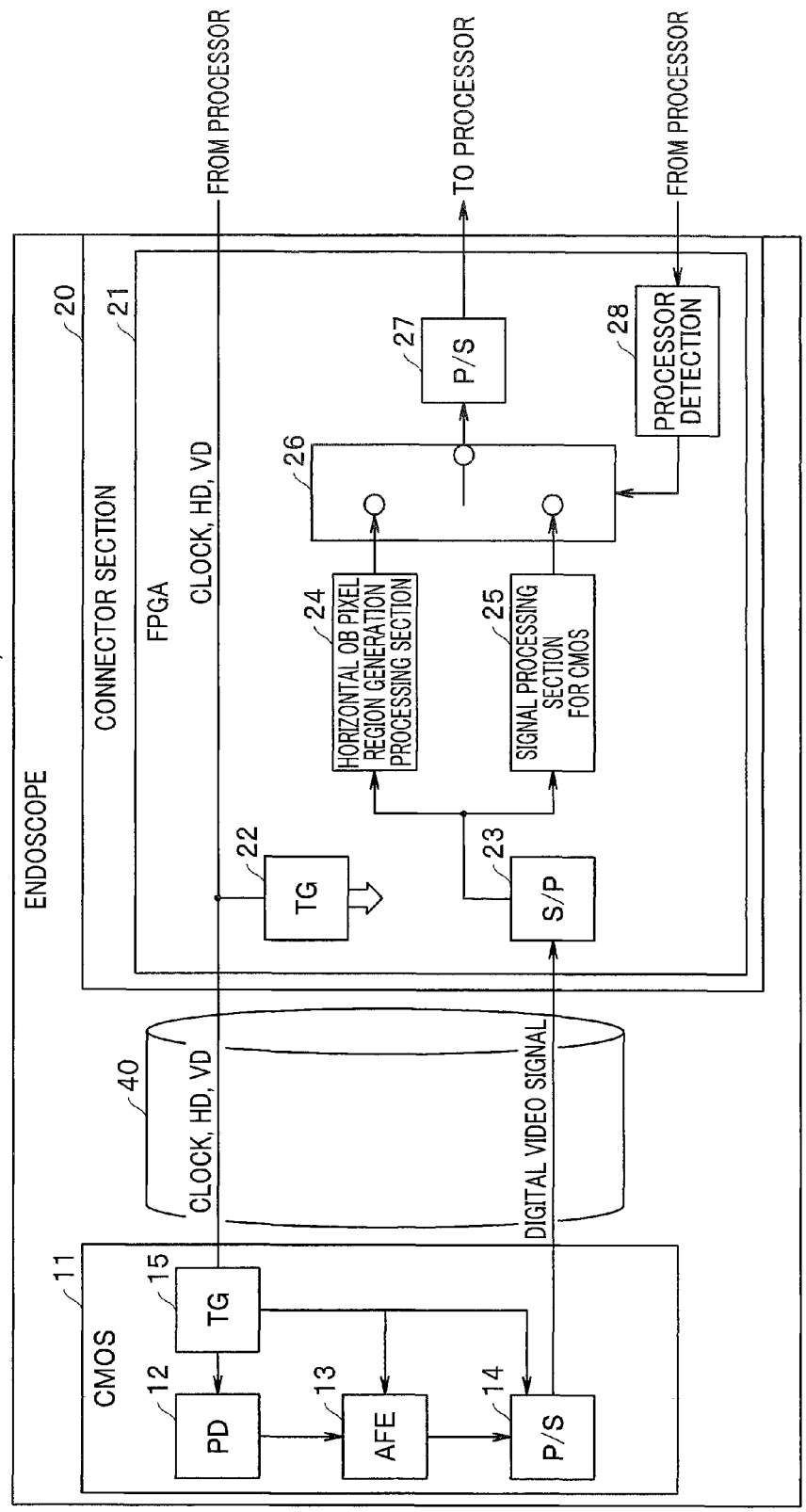
FIG. 1 illustrates a configuration of an endoscope according to a first embodiment of the present invention.

As shown in FIG. 1, an endoscope 1 according to a first embodiment of the present invention includes: a CMOS image sensor 11 which is provided at the distal end of an insertion portion to be inserted into a subject and which is configured to pick up an optical image of the subject to output a predetermined digital image pickup signal; a cable 40 connected to the CMOS image sensor 11 and configured to transmit the digital image pickup signal; and a connector section 20 connected to a processor (to be detailed later) as a signal processing apparatus that performs predetermined signal processing.

The CMOS image sensor 11 includes: a timing generator (TG) 15 that generates, based on a predetermined clock signal and synchronization signals HD, VD transmitted from a clock synchronization signal generation circuit 31 in the processor 3 (see FIG. 8), a clock signal, a horizontal synchronization signal HD and a vertical synchronization signal VD, and pulses for various kinds of signal processing in accordance with an operation specification of the CMOS image sensor 11; an image pickup section 12 (PD 12) that picks up an optical image of a subject to generate a predetermined analog image pickup signal, based on the clock signal, the horizontal synchronization signal HD, and the vertical synchronization signal VD which have been generated in the timing generator 15; an AFE circuit 13 which performs predetermined signal processing on the image pickup section 12 and which includes an A/D conversion section for converting the analog image pickup signal into a digital image pickup signal and outputting the digital image pickup signal; and a P/S circuit 14 that performs parallel/serial conversion on the digital image pickup signal outputted from the AFE circuit 13, to output the signal subjected to the parallel/serial conversion to a subsequent stage.

Note that the AFE circuit 13 includes a CDS circuit that performs predetermined correlated double sampling processing on the analog image pickup signal outputted from the image pickup section 12, and an A/D conversion circuit that performs A/D conversion on the analog image pickup signal subjected to the correlated double sampling processing and outputs the resultant signal.

The cable 40 transmits the predetermined clock signal and synchronization signals HD, VD which are transmitted from the processor 3 to the CMOS image sensor 11, and transmits the digital image pickup signal, which is a serial signal obtained by the parallel/serial conversion in the P/S circuit 14, to an S/P conversion circuit 23 provided in the connector section 20.

In the present embodiment, in the connector section 20, a circuit that performs predetermined signal processing on the digital image pickup signal is configured by an FPGA (field-programmable gate array) (hereinafter, FPGA 21).

The FPGA 21 receives the clock signal and synchronization signals HD, VD, which have been generated in the processor 3, to output the received signals to the CMOS image sensor 11.

The FPGA 21 includes: a timing generator (TG) 22 that generates pulses for various kinds of signal processing based on the clock signal generated in the processor 3; the S/P conversion circuit 23 that performs serial/parallel conversion on the digital image pickup signal which is the serial signal outputted from the CMOS image sensor 11; a horizontal optical black pixel region generation processing section 24 (hereinafter, referred to as horizontal OB pixel region generation processing section 24) connected to the S/P conversion circuit 23; and a signal processing section for CMOS processor 25 (hereinafter, referred to as signal processing section for CMOS 25) connected also to the S/P conversion circuit 23.

Note that the type of the CMOS image sensor 11 is supposed to be the one in which the optical black pixel region is provided only in the vertical direction in the pixel array region (only the vertical OB pixel region is provided) in the present embodiment.

Referring back to FIG. 1, the FPGA 21 further includes: a signal path switching section 26 that switches the output signal path between the horizontal OB pixel region generation processing section 24 and the signal processing section for CMOS processor 25; a P/S circuit 27 that performs parallel/serial conversion on the output signal from the signal path switching section 26 and outputs the resultant signal to the processor; and a processor detection circuit 28 that causes the signal path in the signal path switching section 26 to be switched according the type of the processor connected with the endoscope 1.

Hereinafter, description will be made on the horizontal OB pixel region generation processing section 24 and the signal processing section for CMOS processor 25.

Figure 4:
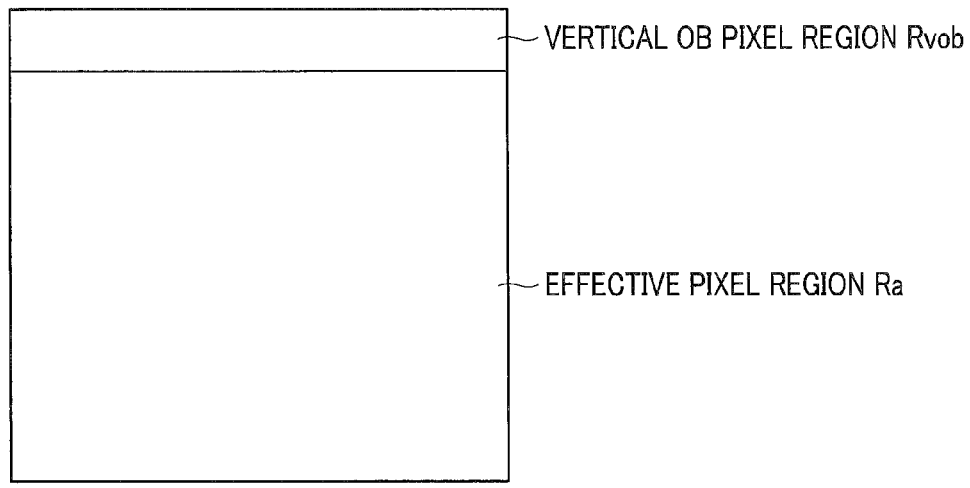
FIG. 4 illustrates a vertical optical black pixel region in the CMOS image sensor of the endoscope according to the first embodiment.

As described above, in the present embodiment, the type of the CMOS image sensor 11 is supposed to be the one in which the optical black pixel region is provided only in the vertical direction in the pixel array region (only the vertical OB pixel region is provided) (see FIG. 4).

That is, as shown in FIG. 4, the CMOS image sensor 11 in the present embodiment includes an effective pixel region Ra where a plurality of pixels that are capable of photoelectrically converting light and generating a photoelectric conversion signal are arranged in a matrix shape, and a vertical optical black pixel region Rvob, which is provided in the upper portion with respect to the scanning direction of the effective pixel region Ra, for performing offset detection of electric charge including dark current.

Note that the vertical optical black pixel region Rvob in the CMOS image sensor 11 is provided in the upper portion with respect to the scanning direction of the effective pixel region Ra in the present embodiment. The present invention, however, is not limited to such a configuration and can be applied to the CMOS image sensor in which the vertical optical black pixel region Rvob is provided in the lower portion or both upper and lower portions with respect to the scanning direction of the effective pixel region Ra.

In contrast, as described above, in the conventional processor adaptive to the endoscope including a CCD image sensor as an image pickup device (hereinafter, referred to as CCD adaptive processor), OB clamp processing geared to the horizontal optical black pixel region (horizontal OB pixel region) in the CCD image sensor is generally performed.

The endoscope according to the present invention has a feature in that the horizontal OB pixel region generation processing section 24 is provided so that, even if the endoscope is connected to the above-described conventional CCD adaptive processor, appropriate image signal processing can be performed in the processor.

Figure 2:
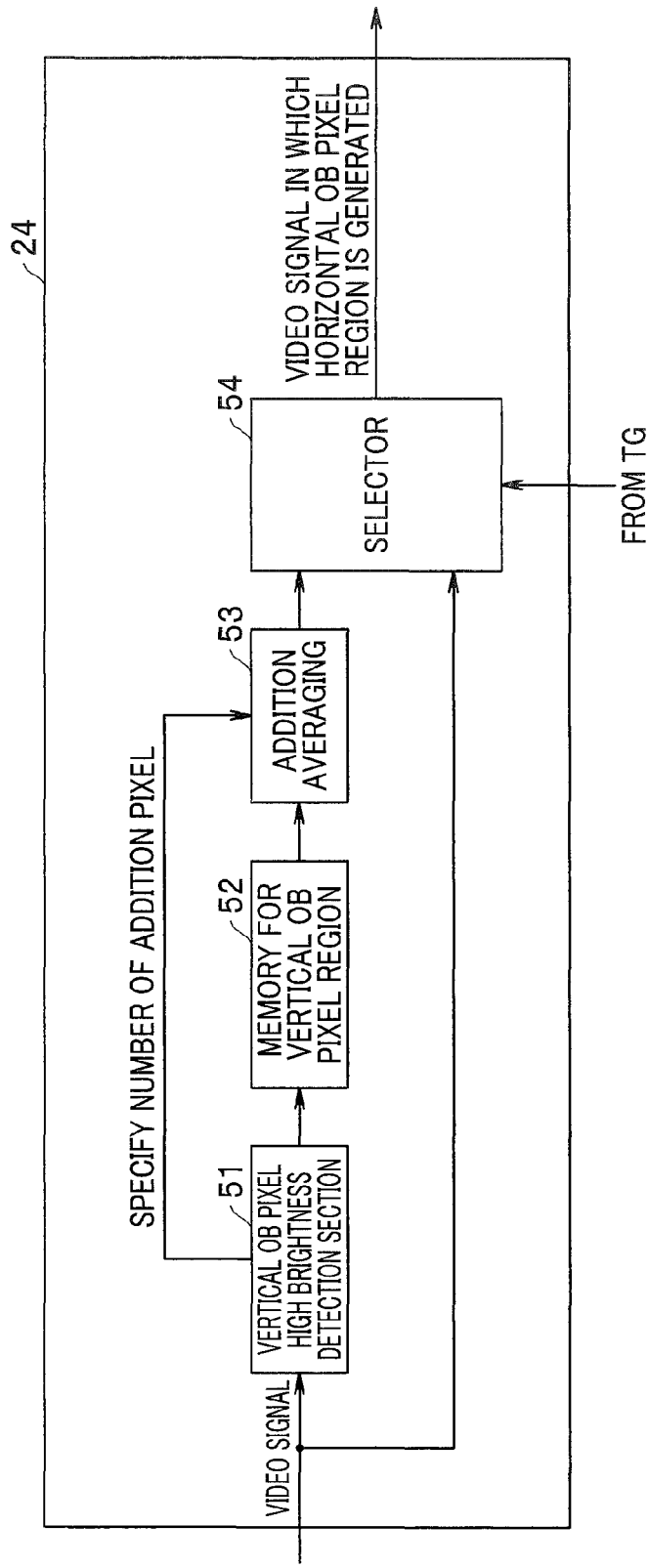
FIG. 2 illustrates a configuration of a horizontal optical black pixel region generation processing section that generates a horizontal optical black pixel region, in the endoscope according to the first embodiment.

FIG. 2 illustrates the configuration of the horizontal OB pixel region generation processing section 24 that generates the horizontal optical black pixel region Rhob in the endoscope according to the present embodiment.

As shown in FIG. 2, the digital image pickup signal (video signal), which is the serial signal obtained as a result of the parallel/serial conversion in the P/S circuit 14 in the CMOS image sensor 11, is inputted to a vertical OB pixel high brightness detection section 51 and a selector 54 in the horizontal OB pixel region generation processing section 24.

The vertical OB pixel high brightness detection section 51 is a reading section that reads the photoelectric conversion signal generated in the effective pixel region Ra (see FIG. 4) in the CMOS image sensor 11 and the optical black signal generated in the vertical optical black pixel region Rvob (see FIG. 4) in the CMOS image sensor 11, for each row.

In addition, the vertical OB pixel high brightness detection section 51 is configured to read an appropriate optical black signal for each row by detecting a white flaw or light leakage from the inputted image pickup signal.

Then, the vertical OB pixel high brightness detection section 51 excludes the pixels whose value is equal to or greater than a set predetermined threshold, and outputs only the signal part corresponding to the pixels which are not affected by the white flaw or light leakage to a memory for vertical OB pixel region 52 in the subsequent stage.

The vertical OB pixel high brightness detection section 51 sends the number of the pixels which are not affected by the white flaw or light leakage as the number of addition pixels to an addition averaging circuit 53.

The memory for vertical OB pixel region 52 once retains the pixel signal not affected by the white flaw and light leakage, which has been inputted from the vertical OB pixel high brightness detection section 51, and then sends the pixel signal to the addition averaging circuit 53.

The addition averaging circuit 53 calculates an addition average value in the vertical optical black pixel region, to send the calculated addition average value to the selector 54 in the subsequent stage.

As described above, the selector 54 receives the digital image pickup signal from the CMOS image sensor 11 and also receives a predetermined pulse signal from the timing generator 22 in the FPGA 21.

Then, the selector 54 adds the optical black signal generated in the vertical optical black pixel region to the photoelectric conversion signal generated in the effective pixel region, which has been read for each row by the vertical OB pixel high brightness detection section 51 as the reading section according to the pulse from the timing generator 22, at a predetermined region of the beginning of the each row in the pixel array region, and outputs the signal to which the optical black signal is added.

In the present embodiment, the predetermined region of the beginning of the respective rows in the pixel array region is set as a newly generated horizontal optical black pixel region.

Then, the selector 54 performs the following selection processing for each row in the pixel array region in accordance with the pulse from the timing generator 22. That is, the selector 54 selects, for the each row, to embed the addition average value calculated in the addition averaging circuit 53 into the horizontal optical black pixel region or to embed the digital image pickup signal directly inputted to the selector 54 into a region other than the horizontal optical black pixel region (that is, effective pixel region).

Figure 5:
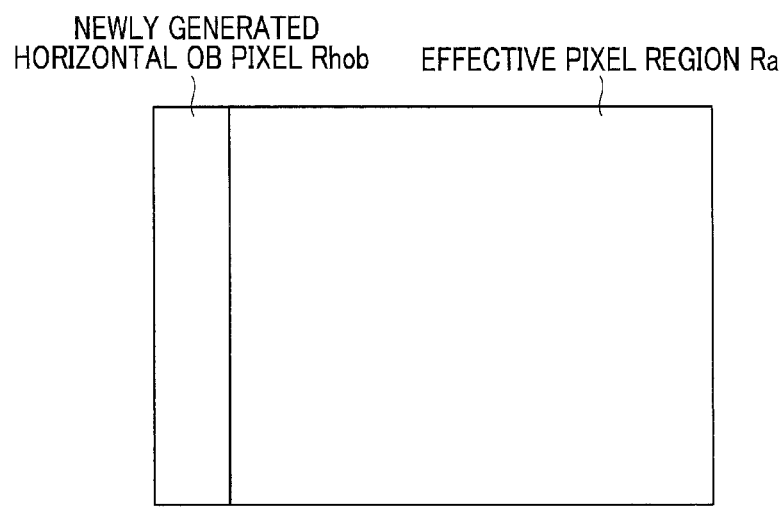
FIG. 5 illustrates a newly generated horizontal optical black pixel region in the endoscope according to the first embodiment.

According to the selection processing by the selector 54, the image pickup signal in which the horizontal optical black pixel region Rhob is newly generated is generated, as shown in FIG. 5.

Note that the horizontal optical black pixel region Rhob is newly generated in the predetermined region of the beginning of the respective rows in the pixel array region in the present embodiment. The present invention, however, is not limited to such a configuration, and the horizontal optical black pixel region Rhob may be newly generated at an arbitrary predetermined region such as the end of the respective rows in the pixel array region so as to be adaptive to a processor which is supposed to be connected to the endoscope.

Furthermore, in the present embodiment, the signal corresponding to the vertical OB pixels detected by the vertical OB pixel high brightness detection section 51 is retained once in the memory for vertical OB pixel region 52 and then sent to the addition averaging circuit 53, and the addition averaging circuit 53 calculates the addition average value in the vertical optical black pixel region, to send the calculated addition average value to the selector 54, as described above. The present invention, however, is not limited to such a configuration.

Figure 3:
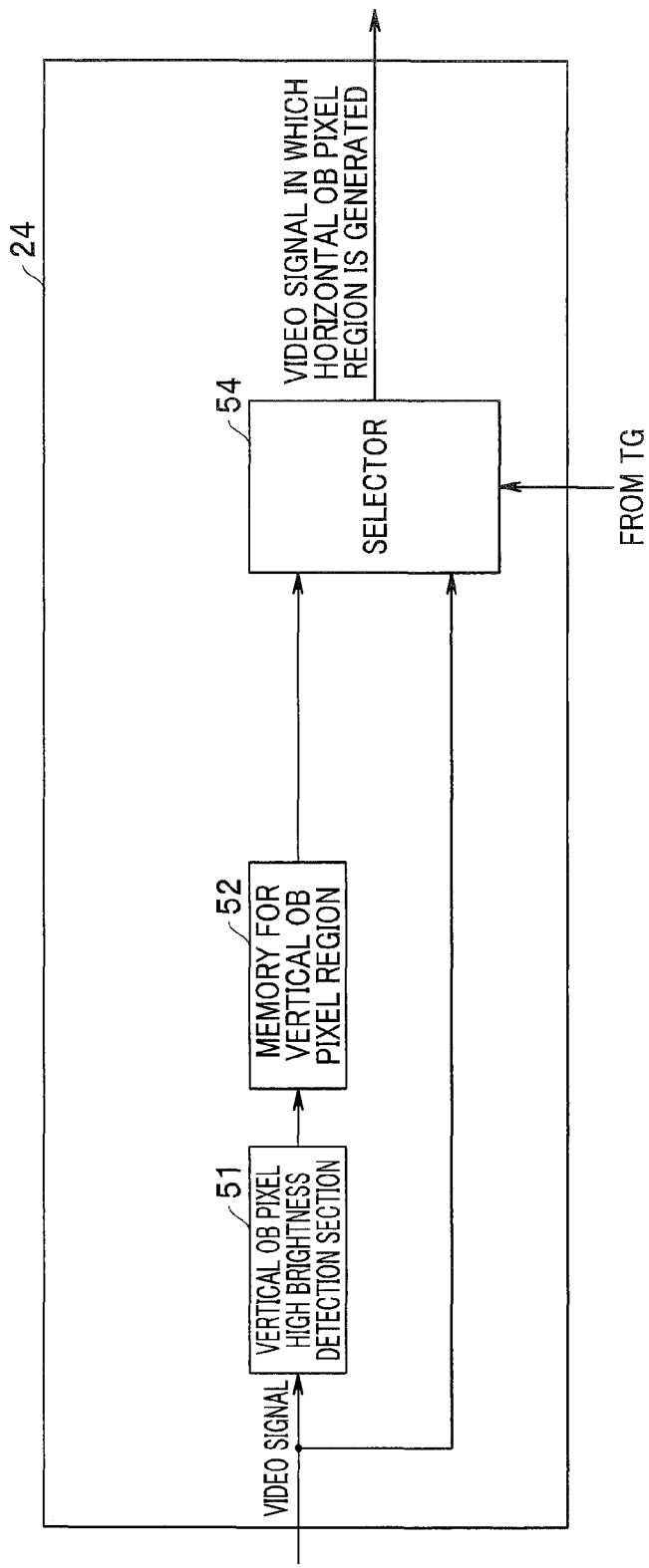
FIG. 3 illustrates another exemplary configuration of the horizontal optical black pixel region generation processing section that generates the horizontal optical black pixel region, in the endoscope according to the first embodiment.

For example, as shown in FIG. 3, the signal corresponding to the vertical OB pixels, which is retained in the memory for vertical OB pixel region 52, may be sent directly to the selector 54, and the selector 54 may perform processing for embedding the signal corresponding to the vertical OB pixels into the horizontal optical black pixel region for each row.

The signal processing section for CMOS processor 25 is different from the horizontal OB pixel region generation processing section 24 in that the signal processing section for CMOS processor 25 is configured to work effectively when the endoscope 1 is connected to a CMOS adaptive processor 3A that performs processing geared to the CMOS image sensor 11 (that is, the CMOS image sensor having only the vertical optical black pixel region).

That is, the signal processing section for CMOS processor 25 allows the image pickup signal to pass through as it is, and sends the image pickup signal to the signal path switching section 26 in the subsequent stage in the present embodiment.

Next, description will be made on the processor 3 and the processor 3A which can be connected with the endoscope 1.

Figure 6:
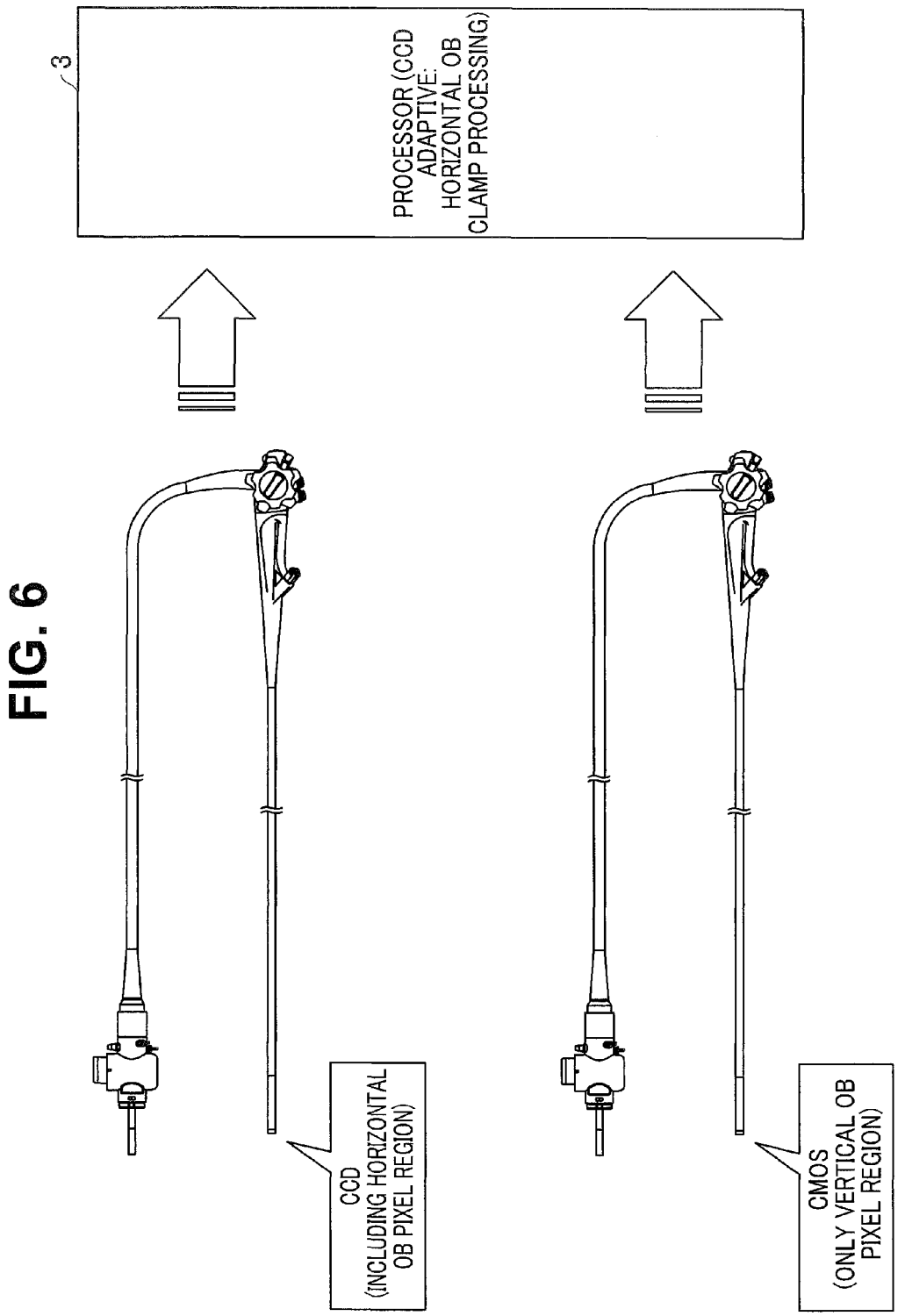
FIG. 6 illustrates a connection relationship between the endoscope according to the first embodiment and a CCD adaptive processor, and a connection relationship between a conventional endoscope and the CCD adaptive processor.

FIG. 6 illustrates a connection relationship between the endoscope according to the present embodiment and the CCD adaptive processor and the connection relationship between the conventional endoscope and the CCD adaptive processor.

As shown in FIG. 6, the processor 3 is a conventional CCD adaptive processor connectable to the endoscope including the CCD image sensor as the image pickup device. However, even if the processor 3 is connected to an endoscope that employs the CMOS image sensor (CMOS image sensor having only the vertical optical black pixel region), as long as the endoscope has the configuration of the endoscope 1 according to the present embodiment as described above, appropriate image signal processing can be performed in the processor.

Figure 8:
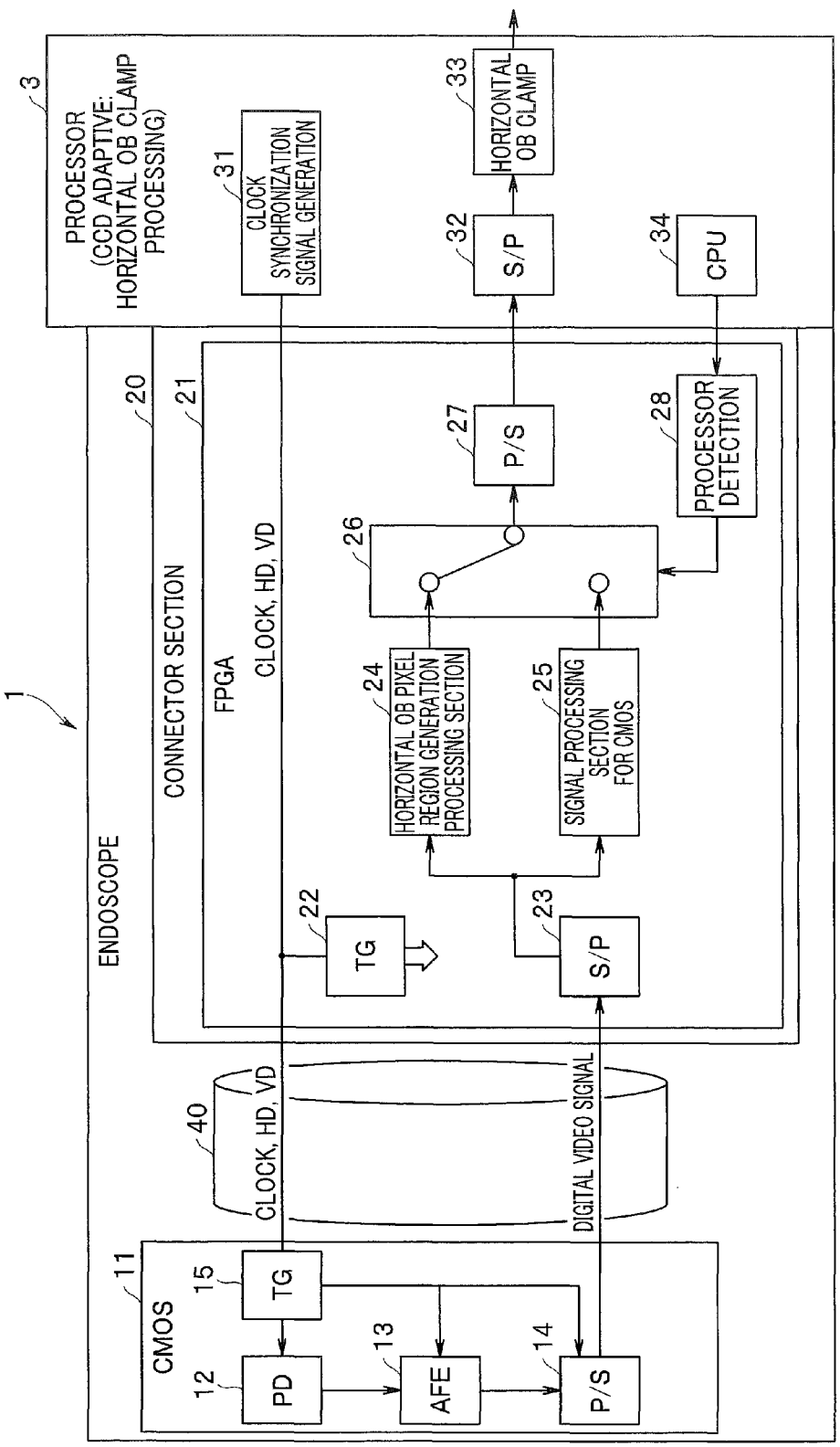
FIG. 8 illustrates a configuration at the time when the endoscope according to the first embodiment is connected to the CCD adaptive processor.

As shown in FIG. 8, the CCD adaptive processor 3 includes: the clock synchronization signal generation circuit 31 that generates a predetermined clock signal and synchronization signals HD, VD; the S/P conversion circuit 32 that performs the serial/parallel conversion on the digital image pickup signal which is the serial signal outputted from the connected endoscope; a horizontal optical black clamp processing circuit 33 connected to the S/P conversion circuit 32; and a CPU 34 that controls various kinds of circuits in the processor 3.

In addition, the CPU 34 in the processor 3 serves to transmit ID information unique to the processor 3 (specifically, information indicating that the processor 3 is the CCD adaptive processor), which is stored in a memory not shown, to the endoscope 1 connected to the processor.

The processor detection circuit 28 in the endoscope 1 according to the present embodiment determines whether or not the connected processor is the CCD adaptive processor, based on the information from the CPU 34 in the connected processor 3.

Note that the above-described processor 3 is supposed to have a function for sending the ID information unique to the processor 3 (information indicating that the processor is the CCD adaptive processor) to the endoscope 1, and the processor detection circuit 28 is supposed to obtain the ID information to determine the type of the connected processor. However, the processor determination method is not limited to the above-described method.

For example, the type of the processor 3 may be determined by non-reception of predetermined ID information from the connected processor.

More specifically, as described later, if the "CMOS adaptive processor" is configured to always send the ID information unique to itself, that is, the information indicating the CMOS adaptive processor, and the CCD adaptive processor such as the processor 3 is configured not to send the ID information for processor determination, determination that the processor 3 is the CCD adaptive processor can be made by non-reception of the ID information.

Referring back to FIG. 8, the horizontal optical black clamp processing in the horizontal optical black clamp processing circuit 33 is known OB clamp processing in which the level of the output signal (optical black signal) from the optical black pixel region is clamped to a predetermined target level, and the average value of the all the optical black signals obtained with the target clamp level as a reference is set as the black level. The CCD adaptive processor 3 performs such processing on the horizontal optical black pixel region in the CCD image sensor.

The endoscope 1 according to the present embodiment is connectable not only to the above-described conventional CCD adaptive processor but also to the processor 3A.

Figure 7:
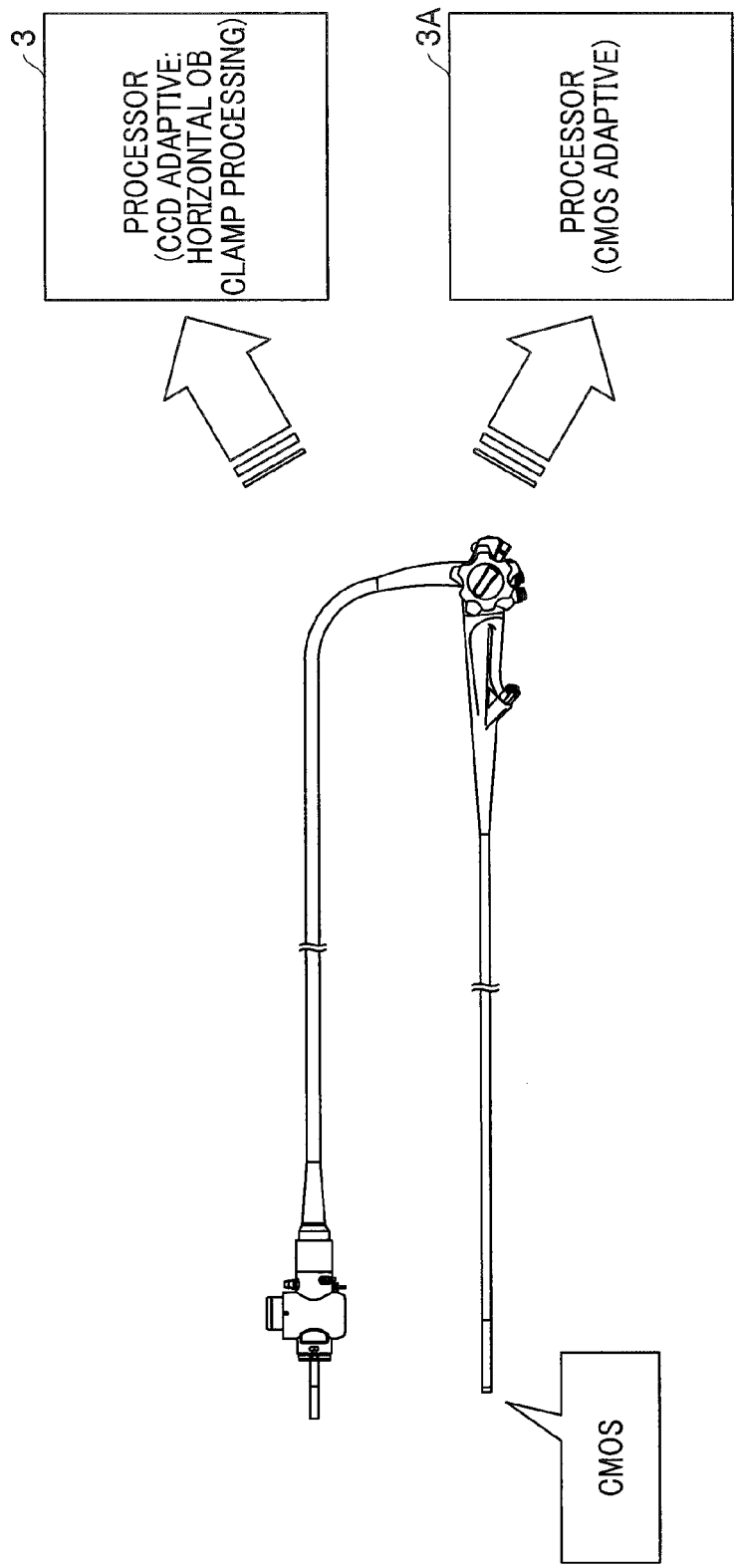
FIG. 7 illustrates a connection relationship between the endoscope according to the first embodiment and the CCD adaptive processor, and a connection relationship between the endoscope according to the first embodiment and a CMOS adaptive processor.

FIG. 7 illustrates a connection relationship between the endoscope according to the present embodiment and the CCD adaptive processor, and a connection relationship between the endoscope according to the present embodiment and the CMOS adaptive processor.

The processor 3A includes a signal processing circuit under the assumption that the endoscope 1 to which the CMOS image sensor 11 (CMOS image sensor having only the vertical optical black pixel region) is mounted is connected to the processor 3A.

Next, description will be made respectively on the working at the time when the endoscope 1 according to the present embodiment is connected to the CCD adaptive processor 3 and the working at the time when the endoscope 1 according to the present embodiment is connected to the CMOS adaptive processor 3A.

Figure 9:
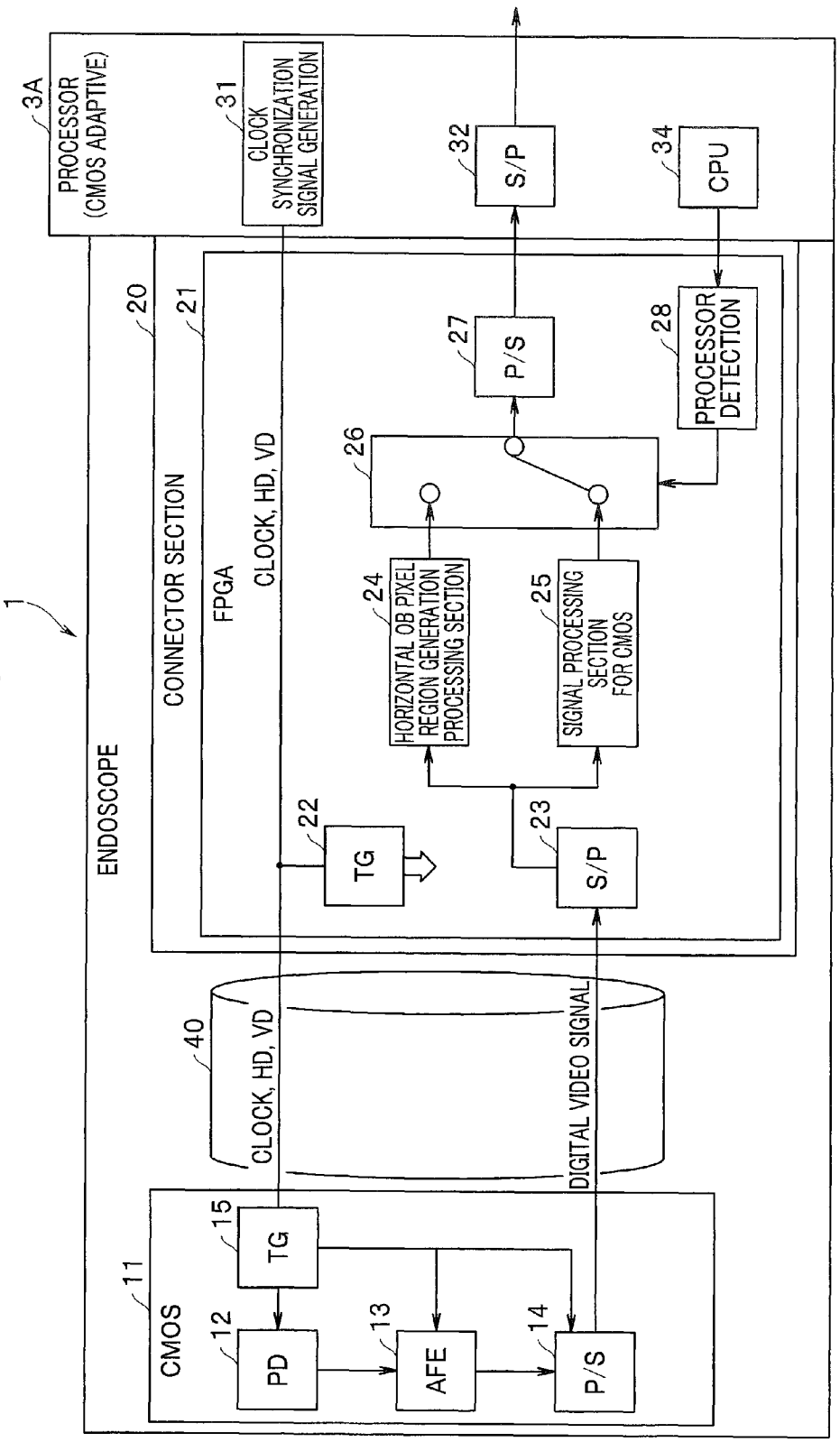
FIG. 9 illustrates a configuration at the time when the endoscope according to the first embodiment is connected to the CMOS adaptive processor.

FIG. 8 illustrates a configuration at the time when the endoscope according to the present embodiment is connected to the CCD adaptive processor 3, and FIG. 9 illustrates a configuration at the time when the endoscope according to the present embodiment is connected to the CMOS adaptive processor 3A. Furthermore, FIG. 10 is a flowchart showing the horizontal optical black pixel region generation processing in the endoscope according to the present embodiment.

Figure 10:
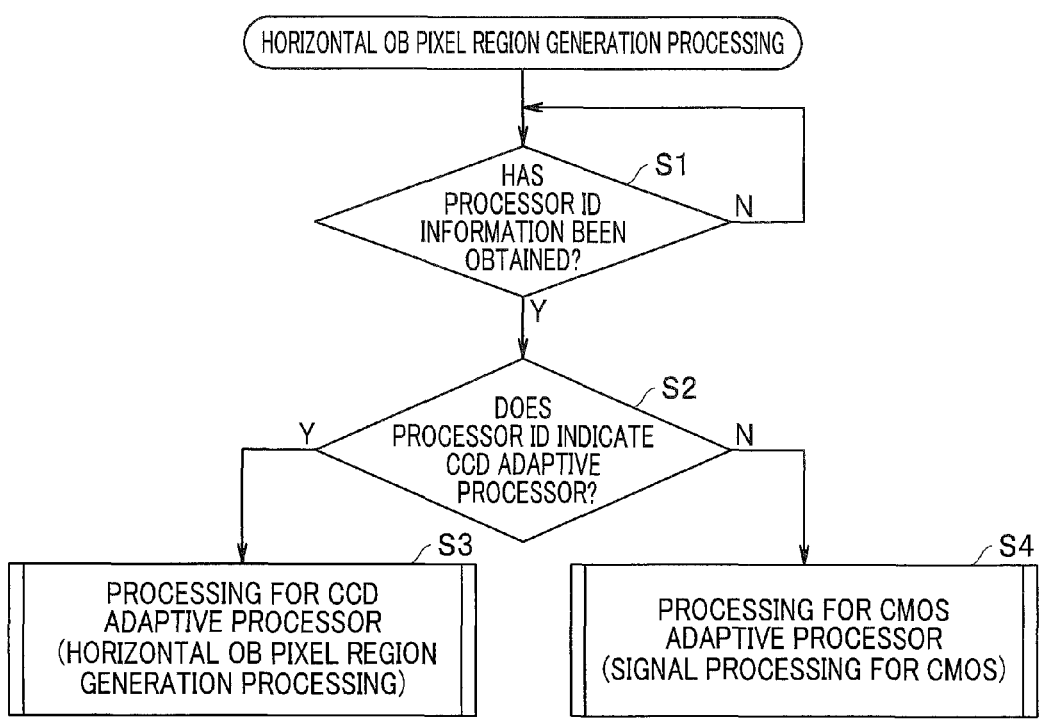
FIG. 10 is a flowchart showing a working of horizontal optical black pixel region generation processing in the endoscope according to the first embodiment.

As shown in FIG. 10, when the processor detection circuit 28 in the endoscope 1 detects that the endoscope 1 is connected to a predetermined processor, the processor detection circuit 28 obtains predetermined ID information from the CPU 34 (see FIGS. 8 and 9) of the connected processor (step S1).

After that, the processor detection circuit 28 determines whether the processor connected with the endoscope 1 is the CCD adaptive processor 3 or the CMOS adaptive processor 3A, based on the ID information obtained in the step S1 (step S2).

Note that the processor detection circuit 28 may determine whether or not the processor 3 is the CCD adaptive processor by the non-reception of the ID information, as described above.

When determining that the connected processor is the CCD adaptive processor 3 in the Step S2, the processor detection circuit 28 performs the processing in step S3.

That is, in the step S3, the processor detection circuit 28 controls the signal path switching section 26 to switch the signal path such that the image pickup signal to be outputted from the P/S circuit 27 is routed through the horizontal optical black pixel region generation processing section 24 (see FIG. 8).

As described above, when the signal path is selected such that the image pickup signal is routed through the horizontal optical black pixel region generation processing section 24, the image pickup signal in which a new horizontal optical black pixel region Rhob is generated is sent from the P/S circuit 27 to the processor 3.

This enables the CCD adaptive processor 3 which receives the above-described image pickup signal to perform the usual horizontal OB clamp processing in the horizontal optical black clamp processing circuit 33 (even if the endoscope connected to the processor 3 is the endoscope 1 to which the CMOS image sensor 11 is mounted).

On the other hand, when determining that the connected processor is the CMOS adaptive processor 3A in step S2, the processor detection circuit 28 performs the processing in step S4.

That is, in the step S4, the processor detection circuit 28 controls the signal path switching section 26 to switch the signal path such that the image pickup signal to be outputted from the P/S circuit 27 is routed through the signal processing section for CMOS processor 25 (see FIG. 9).

As described above, the signal processing section for CMOS processor 25 allows the image pickup signal to pass through as it is, and sends the image pickup signal to the signal path switching section 26 in the subsequent stage in the present embodiment. Therefore, appropriate signal processing can be performed also in the CMOS adaptive processor 3A.

According to the present embodiment, as described above, it is possible to provide an endoscope which employs the CMOS image sensor including only the vertical OB pixel region and which is capable of performing appropriate image signal processing in the processor, even if the endoscope is connected to the processor provided with only the OB clamp processing circuit geared to the horizontal optical black pixel region.

Note that the FPGA 21 is disposed in the connector section 20 in the present embodiment. The present invention, however, is not limited to such a configuration, and the FPGA 21 may be disposed in the operation portion and the like in the endoscope 1.

In addition, as described above, the vertical optical black pixel region Rvob in the CMOS image sensor 11 is provided in the upper portion with respect to the scanning direction of the effective pixel region Ra in the present embodiment. The present invention, however, is not limited to such a configuration, and can be applied to the CMOS image sensor in which the vertical optical black pixel region Rvob is provided in the lower portion with respect to the scanning direction of the effective pixel region Ra.

Further, in the present embodiment, the horizontal optical black pixel region Rhob is newly generated at the predetermined region of the beginning of the respective rows in the pixel array region. The present invention, however, is not limited to such a configuration, and the horizontal optical black pixel region Rhob is newly generated at the predetermined region of the end of the respective rows in the pixel array region.

Furthermore, in the present embodiment, the CMOS image sensor is assumed as the image pickup device of the endoscope 1. However, the image sensor is not limited to the CMOS image sensor, and the present invention can be applied to the endoscope that employs an image pickup device having only a vertical optical black pixel region.

Next, description will be made on the second embodiment of the present invention.

Figure 11:
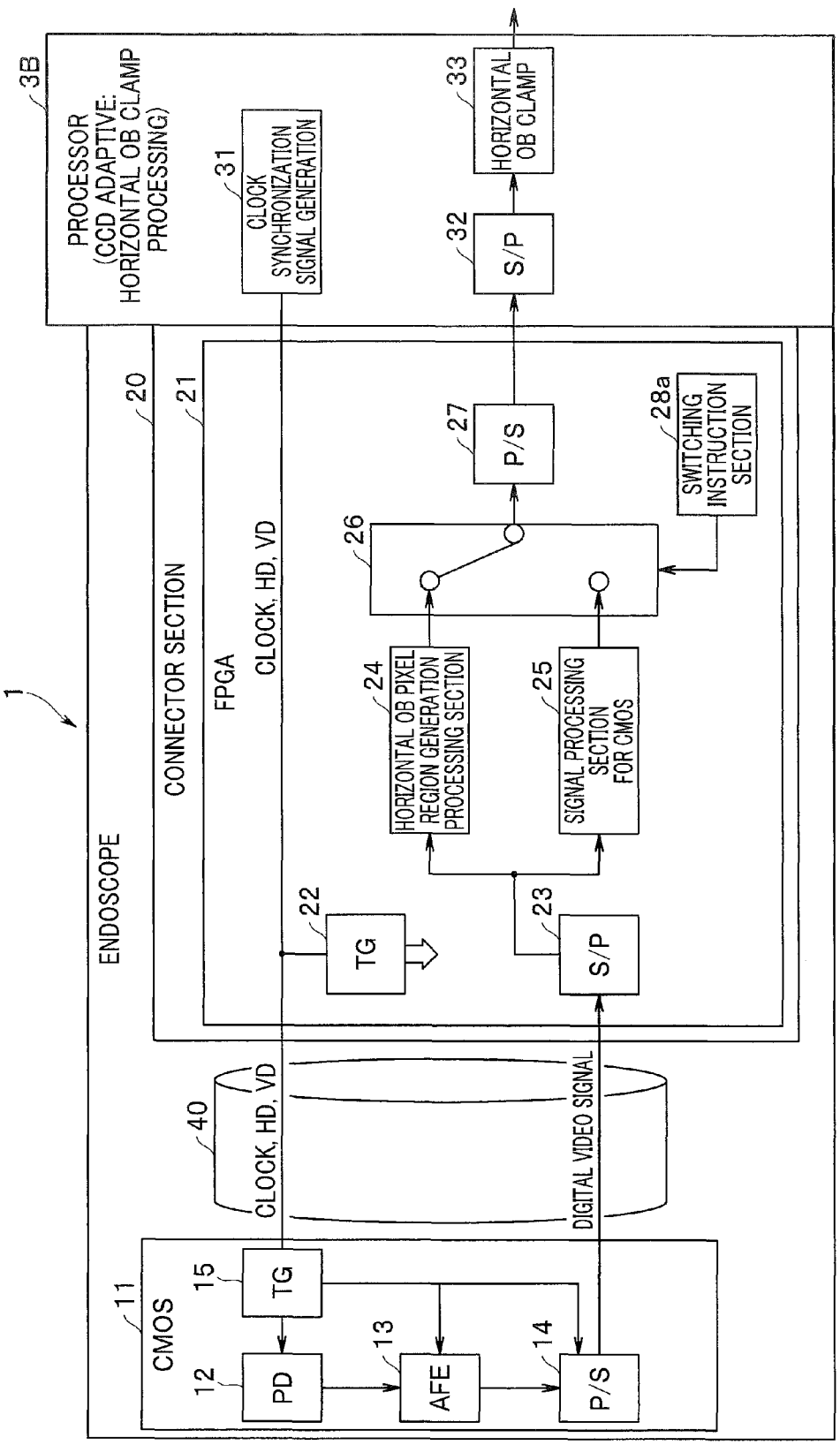
FIG. 11 illustrates a configuration at the time when an endoscope according to a second embodiment of the present invention is connected to the CCD adaptive processor.
Figure 12:
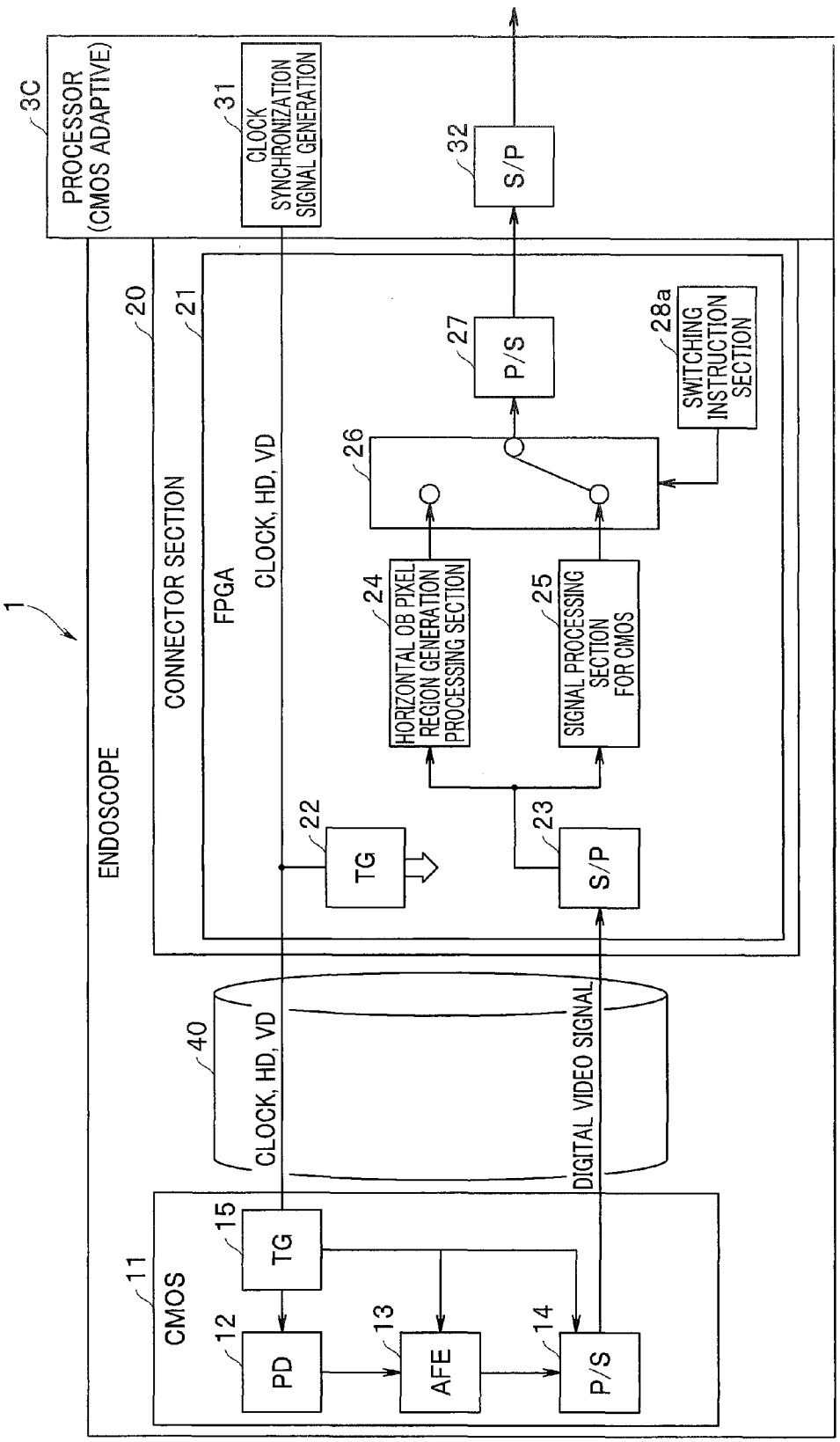
FIG. 12 illustrates a configuration at the time when the endoscope according to the second embodiment is connected to the CMOS adaptive processor.
Figure 13:
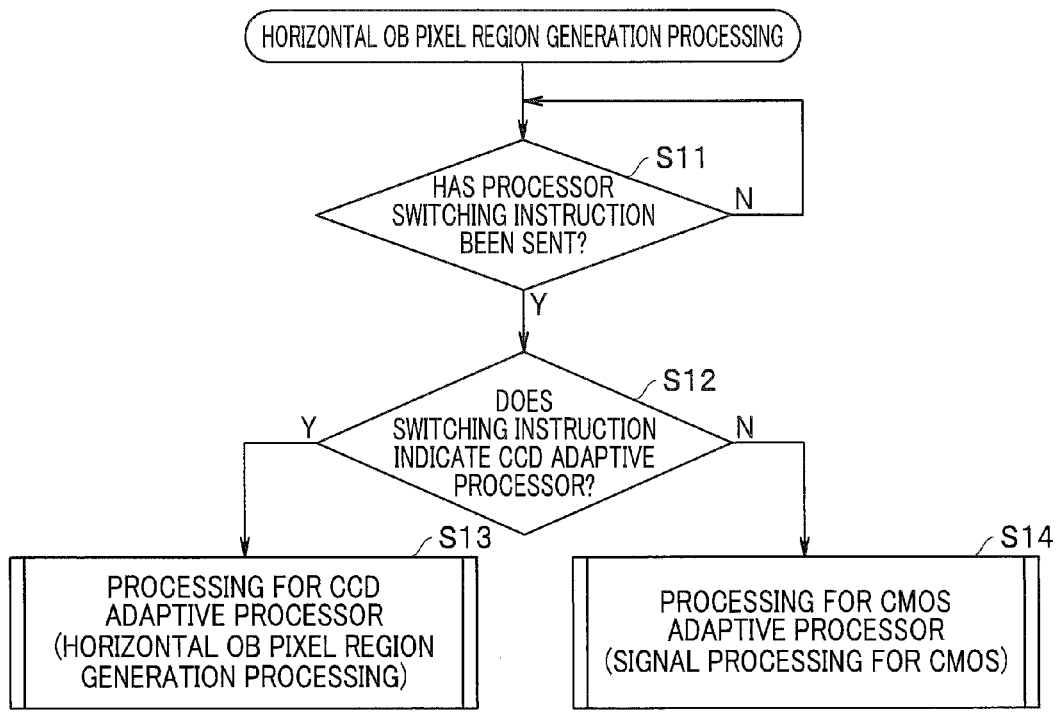
FIG. 13 is a flowchart showing a working of horizontal optical black pixel region generation processing in the endoscope according to the second embodiment.

FIG. 11 illustrates a configuration at the time when an endoscope according to the second embodiment of the present invention is connected to the CCD adaptive processor, and FIG. 12 illustrates a configuration at the time when the endoscope according to the second embodiment is connected to the CMOS adaptive processor. Further, FIG. 13 is a flowchart showing a working of the horizontal optical black pixel region generation processing in the endoscope according to the second embodiment.

The endoscope system according to the second embodiment has a basic configuration same as that in the first embodiment, but different from the endoscope system in the first embodiment only in a part of configuration in the FPGA 21 of the connector section 20. Therefore, description will be made only on the difference between the present embodiment and the first embodiment, and description on the parts common to both embodiments will be omitted.

In the above-described first embodiment, the FPGA 21 includes the processor detection circuit 28 that causes the signal path in the signal path switching section 26 to be switched according to the type of the processor connected to the endoscope 1 (see FIG. 1). In contrast, as shown in FIGS. 11, 12, the second embodiment has a feature in that a switching instruction section 28*a* that sends a switching instruction signal for switching the signal path in the signal path switching section 26 is provided instead of the processor detection circuit 28.

The switching instruction section 28*a* sends the switching instruction signal to the signal path switching section 26 by an operation, not shown (for example, setting by a user). The switching instruction signal is an instruction signal for switching the signal path between a first signal path in which the digital image pickup signal passes through the horizontal optical black pixel region generation processing section 24 and a second signal path in which the digital image pickup signal passes through the signal processing section for CMOS processor 25 (that is, the signal path in which the digital image pickup signal does not pass through the horizontal optical black pixel region generation processing section).

In addition, in the second embodiment, the signal path switching section 26 switches the signal path between the first signal path and the second signal path according to the switching instruction signal from the switching instruction section 28*a*.

Thus, in the second embodiment, the above-described switching of the signal paths can be performed without the need for detecting the type of the processor (CCD adaptive processor 3B (see FIG. 11) or CMOS adaptive processor 3C (see FIG. 12)) connected with the endoscope 1.

Next, description will be made respectively on the working at the time when the endoscope 1 according to the present embodiment is connected to the CCD adaptive processor and the working at the time when the endoscope 1 according to the present embodiment is connected to the CMOS adaptive processor.

As shown in FIG. 13, when the switching instruction signal is sent from the switching instruction section 28*a* in the endoscope 1 (step S11), the signal path switching section 26 switches the signal path between the first signal path and the second signal path, based on whether the switching instruction signal from the switching instruction section 28*a* indicates the CCD adaptive processor 3B or the switching instruction signal indicates the CMOS adaptive processor 3C (step S12).

That is, when the switching instruction signal indicates the CCD adaptive processor 3B (in other words, the switching signal indicates the processor in which the horizontal optical black clamp processing circuit 33 works with respect to the image pickup signal), the signal path switching section 26 selects the first signal path in which the image pickup signal passes through the horizontal optical black pixel region generation processing section 24 (step S13).

On the other hand, when the switching instruction signal indicates the CMOS adaptive processor 3C, the signal path switching section 26 selects the second signal path in which the image pickup signal passes through the signal processing section for CMOS processor 25 (step S14).

As described above, according to the present embodiment, it is possible to provide an endoscope which includes the CMOS image sensor and which is capable of performing appropriate image signal processing in the processor, even if the endoscope is connected to the processor including the horizontal optical black clamp processing circuit without detecting the type of the processor to be connected.

As described above, according to the present embodiment, it is possible to provide an endoscope which includes the CMOS image sensor and which is capable of performing appropriate image signal processing in the processor, even if the endoscope is connected to the processor including a signal processing circuit configured to perform processing for enhancing the high frequency components on an image pickup signal without detecting the type of the processor to be connected.

Note that the present invention is not limited to the above-described embodiments as they are, and can be embodied by modifying the constituent elements in the practical stage without departing from the gist of the invention. Furthermore, various aspects of the invention can be implemented by appropriately combining a plurality of constituent elements disclosed in the embodiments. For example, some constituent elements may be deleted from all the constituent elements shown in the embodiments. Furthermore, constituent elements over different embodiments may be appropriately combined.

Thus, it is needless to say that various changes or applications are possible without departing from the gist of the invention.

What is claimed is:

1. An endoscope comprising:
an image sensor including an effective pixel region in which a plurality of pixels capable of photoelectrically converting light to generate a photoelectric conversion signal are provided in a matrix shape, and a vertical optical black pixel region provided in at least one of an upper portion or a lower portion with respect to a scanning direction of the effective pixel region, wherein the image sensor does not include an optical black pixel region arranged in a direction perpendicular to the vertical optical black pixel region;
one or more processors comprising hardware, the one or more processors being configured to:
read the photoelectric conversion signal generated in the effective pixel region in the image sensor and one or more optical black signals generated in the vertical optical black pixel region in the image sensor;
add the one or more optical black signals generated in the vertical optical black pixel region to a predetermined region in each row of the photoelectric conversion signal which has been generated in the effective pixel region and read for each row, such that a horizontal optical black pixel region arranged in a column direction of the plurality of pixels is newly formed; and
output a signal generated by adding the one or more optical black signals to the predetermined region in each row of the photoelectrical conversion signal.

2. The endoscope according to claim 1, wherein to add the one or more optical black signals to the predetermined region in each row of the photoelectric conversion signal, the one or more processors are further configured to:
compare a value of each of the one or more optical black signals read from the vertical optical black pixel region with a predetermined threshold;
extract the one or more optical black signals each which has a value smaller than the predetermined threshold, based on the comparison result; and
add the one or more optical black signals having the value smaller than the predetermined threshold to the predetermined region of each row of the photoelectric conversion signal.

3. The endoscope according to claim 2, wherein to add the one or more optical black signals to the predetermined region in each row of the photoelectric conversion signal, the one or more processors are further configured to:
add and average the one or more optical black signals each having the value smaller than the predetermined threshold to generate an addition average value; and
add the addition average value of the one or more optical black signals to the predetermined region of each row of the photoelectric conversion signal.

4. The endoscope according to claim 1, wherein the endoscope is connectable to a first processor provided with a clamp circuit that performs clamp processing geared to the horizontal optical black pixel region.

5. The endoscope according to claim 4, wherein
the endoscope is further connectable to a second processor which is not provided with the clamp circuit, the second processor being different from the first processor, and the endoscope further comprises:
another processor including hardware identifying whether the endoscope is connected to the first processor or the second processor; and
a signal path switch configured to switch a signal path between a first signal path in which the one or more optical signals and the photoelectric conversion signal from the image sensor are read or added using the one or more processors and a second signal path in which the one or more optical signals and the photoelectric conversion signal are not read and added using the one or more processors, based on an identification result by the another processor.

6. The endoscope according to claim 5, wherein, based on the identification result by the another processor, the signal path switch switches the signal path of the one or more optical signals and the photoelectric conversion signal to the first signal path when the endoscope is connected to the first processor and switches the signal path of the one or more optical signals and the photoelectric conversion signal to the second signal path when the endoscope is connected to the second processor.

7. The endoscope according to claim 4, wherein
the endoscope is further connectable to a second processor which is not provided with the clamp circuit, the second processor being different from the first processor, and
the endoscope further includes:
other processor including hardware outputting a switching instruction signal for switching a signal path between a first signal path in which the one or more optical signals and the photoelectric conversion signal from the image sensor are read and added using the one or more processors and a second signal path in which the one or more optical signals and the photoelectric conversion signal are not read and added using the one or more processors; and
a signal path switch switches the signal path between the first signal path and the second signal path based on the switching instruction signal.

* * * * *